United States Patent

Tomiyama et al.

Patent Number: 5,843,999
Date of Patent: Dec. 1, 1998

[54] 2-PHENYLAZULENE DERIVATIVES AND A MANUFACTURING METHOD OF THESE COMPOUNDS

[75] Inventors: Tsuyoshi Tomiyama; Akira Tomiyama, both of Nagano-ken; Masayuki Yokota, Koushoku; Satoko Uchibori, Nagano-ken, all of Japan

[73] Assignee: Kotobuki Seiyaku Co., Ltd., Nagano-ken, Japan

[21] Appl. No.: 982,639

[22] Filed: Dec. 2, 1997

[30] Foreign Application Priority Data

Dec. 2, 1996 [JP] Japan ................................. 8-321894

[51] Int. Cl.$^6$ ................ A61K 31/235; A61K 31/19; A61K 31/110; A61K 31/18
[52] U.S. Cl. ............... 514/602; 514/530; 514/569; 514/570; 514/573; 514/709; 514/886; 514/887; 514/916; 560/10; 562/427; 564/84; 564/89; 568/33; 568/34
[58] Field of Search ......................... 514/530, 569, 514/570, 573, 602, 709, 886, 887, 916; 560/10; 562/427; 564/84, 89; 568/33, 34

Primary Examiner—Peter O'Sullivan
Attorney, Agent, or Firm—Sherman and Shalloway

[57] ABSTRACT

A series of new azulene derivatives are disclosed, which are represented by the following formula;

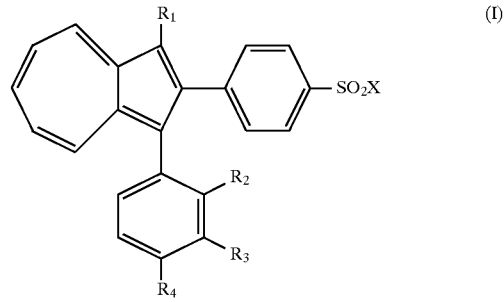

wherein: $R_1$ is hydrogen atom, lower alkoxycarbonyl group, carboxy group, halogen atom, lower alkyl group, phenyl group or lower alkanoyl group; $R_2$, $R_3$ and $R_4$ are hydrogen atom, lower alkyl group, lower alkoxy group or halogen atom; X is lower alkyl group or amino group.

The compounds of the present invention are useful for treatment of inflammation.

11 Claims, No Drawings

2-PHENYLAZULENE DERIVATIVES AND A MANUFACTURING METHOD OF THESE COMPOUNDS

BACKGROUND OF THE INVENTION

1. Field of the invention

This invention relates to the novel azulene derivatives which have a cyclooxygenase-2 inhibitory action, the pharmaceutically acceptable salt thereof and the production methods thereof, further relates to a medicine composition containing said the azulene derivatives or the salt thereof.

2. Description of the prior art

Inflammation is the process of disorders which are characterized by flushing, fever, swelling and pain. Arthritis is the frequently generated inflammation disorder and is the most severely disorder. Wound and infectious disease are also involved the inflammation.

Non-steroidal antiinflammatory drugs (NSAIDs) represented by aspirin and indomethacin have been widely used for treatment by inflammation. The therapeutic effect of NSAIDs is related to their capacity to inhibition of the formation of prostaglandins (PGs) via the cyclooxygenase (COX) pathway. However, the most common NSAIDs can produce side effect such as gastrointestinal irritation and suppression of renal function by the inhibition of COX enzyme, that may limit therapeutic potential.

Recently, two distinct forms of COX enzyme were distinguished, a constitutive COX-1 enzyme and an inducible from of the enzyme, now commonly known as COX-2. The COX-1 enzyme is expressed in normal tissues, while COX-2 enzyme is found to be located primary in inflamed tissues. Accordingly, it seems reasonable that a selective COX-2 inhibitor could block PG production at the site of inflammation without NSAIDs—associated side effects (Meneki to Ensho, 3 (1995). Nature, 367 215 (1994). Drug News and Perspectives, 8, 501, 1994).

Due to the novelty of this approach, the literature contains examples of selective or specific COX-2 inhibitors. Gans et al. have reported that the thiophene derivative of formula (XXVI) (J. Pat. No. 58-159489).

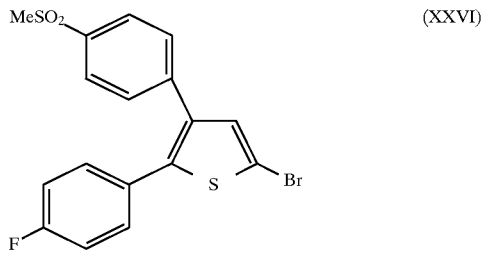

(XXVI)

Similarly, Futaki et al. have reported that the methanesulfonamide derivative of formula (XXVII) (J. Pat. No. 2-300122).

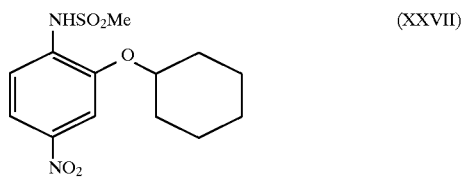

(XXVII)

Furthermore, two groups have reported that the compounds of formula (XXVIII) and (XXIX) are selective COX-2 inhibitors (WO. Pat. No. 9515318 and U.S. Pat. No. 5,510, 368.).

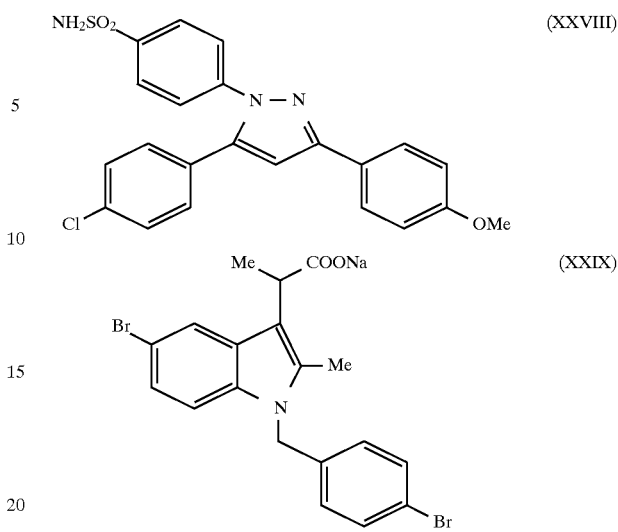

OBJECT OF THE INVENTION

The principal object of the present invention is the provision of novel compounds having antiinflammatory activity via the inhibition of the COX-2. Another object of the present invention is the provision of pharmaceutical compositions useful as antiinflammatory agents. Still other object of the present invention is the provision of new azulene derivatives and a method of the manufacture thereof. These and other objects of the invention will became apparent from the description that follows hereinafter.

BRIEF SUMMARY OF THE INVENTION

This invention related to a series of new azulene derivatives which are antiinflammatory agents. Compounds of formula (I) are selective COX-2 inhibitors and are useful as antiinflammatory agents with the additional benefit of having significantly less harmful side effects. Compounds of formula (I) would be useful for the treatment of inflammation in a subject, and for treatment of other inflammation-associated disorders as an analgesic in the treatment of pain and headaches, or as an antipyretic for the treatment of fever.

The present invention provides the new azulene derivatives of general formula (I)

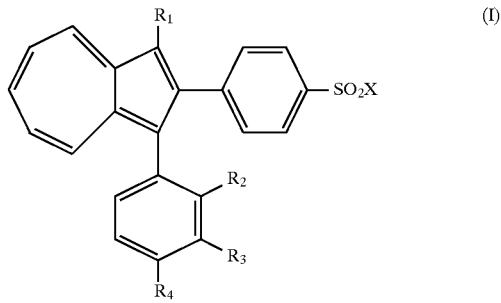

(I)

wherein: $R_1$ is hydrogen atom, lower alkoxycarbonyl group, carboxy group, halogen atom, lower alkyl group, phenyl group or lower alkanoyl group; $R_2$, $R_3$ and $R_4$ are hydrogen atom, lower alkyl group, lower alkoxy group or halogen atom; X is lower alkyl group or amino group.

and its salt capable of being used for medical treatment. In this invention, "lower" means straight or branched $C_1$–$C_5$.

DETAILED DESCRIPTION OF THE INVENTION

A class of compounds of particular interest consists of those compounds of formula (I) wherein $R_1$ is hydrogen atom, methyl group, ethyl group, propyl group, butyl group, pentyl group, phenyl group, fluorine atom, chlorine atom, bromine atom, acetyl group, propionyl group, butyroyl group, pentyloxy group, methoxycarbonyl group, ethoxycarbonyl group, propyloxycarbonyl group, butoxycarbonyl group, pentyloxycarbonyl group and carboxy group; wherein $R_2$, $R_3$ and $R_4$ are hydrogen atom, methyl group, ethyl group, propyl group, butyl group, pentyl group, methoxy group, ethoxy group, propyloxy group, butoxy group, pentyloxy group, fluorine atom, chlorine atom, bromine atom; wherein X is methyl group, ethyl group, propyl group, butyl group, pentyl group and amino group; or a pharmaceutically acceptable salt thereof.

Some compounds fallen within the general formula (I) are as follows.

[1] 2-(4-Methylsulfonylphenyl)-1-phenylazulene.
[2] 1-(2-Chlorophenyl)-2-(4-methylsulfonylphenyl)azulene.
[3] 1-(3-Chlorophenyl)-2-(4-methylsulfonylphenyl)azulene.
[4] 1-(4-Chlorophenyl)-2-(4-methylsulfonylphenyl)azulene.
[5] 1-(3-Fluorophenyl)-2-(4-methylsulfonylphenyl)azulene.
[6] 1-(4-Fluorophenyl)-2-(4-methylsulfonylphenyl)azulene.
[7] 1-(3-Methylphenyl)-2-(4-methylsulfonylphenyl)azulene.
[8] 1-(4-Methylphenyl)-2-(4-methylsulfonylphenyl)azulene.
[9] 1-(3-Methoxyphenyl)-2-(4-methylsulfonylphenyl)azulene.
[10] 1-(4-Methoxyphenyl)-2-(4-methylsulfonylphenyl)azulene.
[11] 1-(3-Chloro-4-fluorophenyl)-2-(4-methylsulfonylphenyl)azulene.
[12] 1-(3-Chloro-4-methylphenyl)-2-(4-methylsulfonylphenyl)azulene.
[13] 1-(3-Chloro4-methoxyphenyl)-2-(4-methylsulfonylphenyl)azulene.
[14] 1-(3-Fluoro-4-methoxyphenyl)-2-(4-methylsulfonylphenyl)azulene.
[15] Methyl 2-(4-methylsulfonylphenyl)-3-phenylazulene-1-carboxylate.
[16] 2-(4-Methylsulfonylphenyl)-3-phenylazulene-1-carboxylic acid.
[17] 3-(3-Chlorophenyl)-2-(4-methylsulfonylphenyl)azulene-1-carboxylic acid.
[18] 3-(3-Chloro-4-methylphenyl)-2-(4-methylsulfonylphenyl)azulene- 1-carboxylic acid.
[19] 3-(3-Chloro-4-methoxyphenyl)-2-(4-methylsulfonylphenyl)azulene-1-carboxylic acid.
[20] 3-(3-Fluoro-4-methoxyphenyl)-2-(4-methylsulfonylphenyl)azulene-1-carboxylic acid.
[21] 1-Fluoro-2-(4-methylsulfonylphenyl)-3-phenylazulene.
[22] 1-Chloro-2-(4-methylsulfonylphenyl)-3-phenylazulene.
[23] 1-Bromo-2-(4-methylsulfonylphenyl)-3-phenylazulene.
[24] 1-Methyl-2-(4-methylsulfonylphenyl)-3-phenylazulene.
[25] 1,3-Diphenyl-2-(4-methylsulfonylphenyl)azulene.
[26] 1-Acetyl-2-(4-methylsulfonylphenyl)-3-phenylazulene.
[27] 4-(1-Phenylazulene-2-yl)phenylsulfonarnide.
[28] 4-[1-(3-Chlorophenyl)azulene-2-yl]phenylsulfonamide.
[29] 4-[1-(3-Fluorophenyl)azulene-2-yl]phenylsulfonamide.
[30] 4-[1-(3-Methylphenyl)azulene-2-yl]phenylsulfonamide.
[31] 4-[1-(3-Methoxyphenyl)azulene-2-yl]phenylsulfonamide.
[32] 4-[1-(3-Chloro-4-fluorophenyl)azulene-2-yl]phenylsulfonamide.
[33] 4-[1-(3-Chloro4-methylphenyl)azulene-2-yl]phenylsulfonamide.
[34] 4-[1-(3-Chloro4-methoxyphenyl)azulene-2-yl]phenylsulfonamide.
[35] 4-[1-(3-Fluoro-4-methoxyphenyl)azulene-2-yl]phenylsulfonamide.
[36] 2-(4-Aminosulfonylphenyl)-3-(3-chloro-4-methoxyphenylazulene-1-carboxylic acid.
[37] [2-(4-Methylsulfonylphenyl)-3-phenylazulene-1-yl]acetic acid.
[38] 1-(3,4-Dimethoxyphenyl)-2-(4-methylsulfonylphenyl)azulene.
[39] 4-[1-(3,4-Dimethoxyphenyl)azulene-2-yl]phenylsulfonamide.

The above mentioned compounds numbered from 1 to 39 will be referred to herein after, as compound 1, compound 2, - - -, compound 39, respectively.

General method of synthesis

The compounds of the invention can be synthesized according to the following procedures of scheme 1–6.

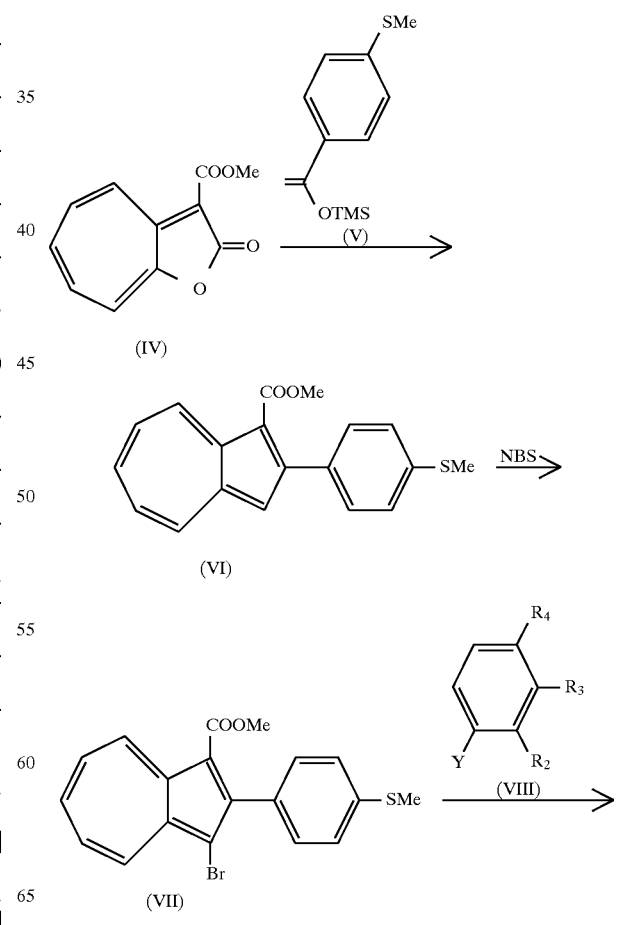

-continued
[Scheme 1]

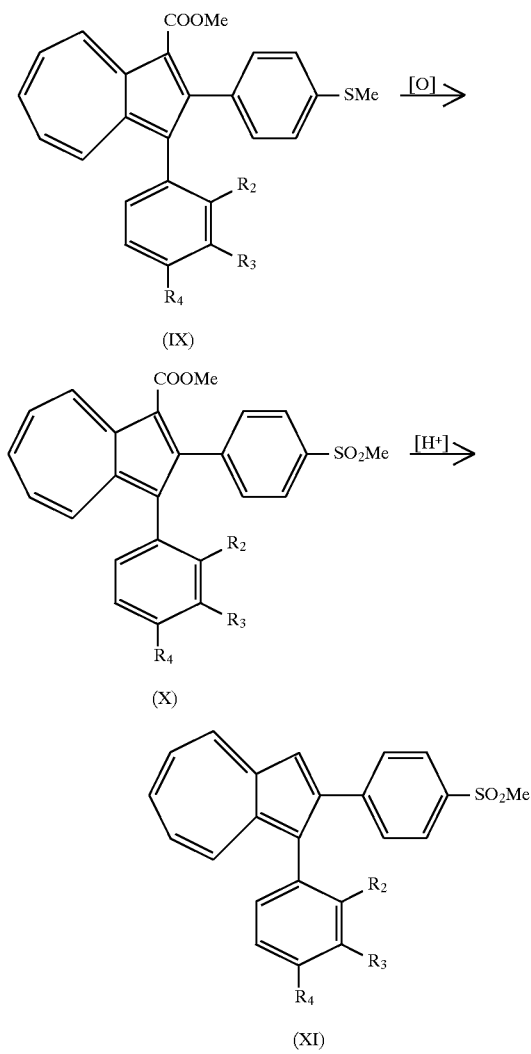

(wherein $R_2$, $R_3$ and $R_4$ are the same as mentioned above; Y is $B(OH)_2$ or $SnMe_3$; TMS represents trimethysilyl)

Scheme 1 shows the preparation of 2-(4-methylsulfonylphenyl)azulene derivatives. Compound (IV), which is a starting material (IV) in this sequence, is synthesized according to the reported methods (Tetrahedron, 27, 6023, 1971). In step 1, compound (IV) is converted into compound (VI) by reaction with silyl enol ether (V). The silyl enol ether (V) is prepared according to the reported methods (Journal of medicinal chemistry, 39, 253, 1996). The preferred reaction temperature for this step is in the range from about 160° C. up to the reflux temperature of the reaction mixture. In step 2, the bromination of compound (VI) using N -bromsuccinimide (NBS) or bromine give the compound (VII). This reaction is carried out in the presence of radical initiators such as α,α'-azobis(isobutyronitrile) and benzoylperoxide in carbon tetrachloride as reaction solvents under the reflux temperature of the reaction mixture. In step 3, compound (VII) is coupled with compound (VIII) to give compound (IX). In the case of Y being $B(OH)_2$ in the formula (VIII), the reaction is carried out using palladium catalyst in the presence of base according to reported methods (Synthetic communications, 11, 513, 1981).

Tetrakis(triphenylphosphine)palladium (0), bis (triphenylphosphine)palladium chloride (2) and palladium chloride (2) can be used as catalysts. This reaction carried out in the presence of base such as sodium hydrogencarbonate, sodium carbonate, sodium methoxide, triethylamine and pyridine. Preferred reaction solvents for use in this coupling reaction include benzenee, toluene, dioxane, tetrahydrofuran, chloroform, methanol, N,N-dimethylformamide and water. In general, this reaction carried out in the range from 80° C. up to 120° C. Alternatively, compound (IX) can be obtained using a tin reagent instead of boronic acid. In the case of Y being $SnMe_3$ in the formula (VIII), the reaction is carried out using palladium catalyst according to reported methods (Angewante chimie, international edition in English, 25, 508, 1986). Tetrakis(triphenylphosphine)palladium (0), bis (triphenylphosphine)palladium chloride (2) and palladium chloride (2) can be used as catalysts. Preferred reaction solvents for use in this coupling include benzenee, toluene, dioxane, tetrahydrofuran, chloroform, methanol, N,N-dimethylformamide and water. In general, this reaction carried out under in the range from 80° C. up to 120° C. In step 4, compound (IX) is oxidized to compound (X) in reaction solvents such as methanol, ethanol, dichloromethane, tetrahydrofuran and water Hydrogen peroxide, m-chloroperbenzoic acid, oxone and sodium periodate are suitable for oxidation and the reaction carried out at a temperature ranging from room temperature up to the reflux temperature of the reaction mixture. In step 5, compound (X) is treated with acids such as sulfuric acid, p-toluenesulfonic acid, trifluoroacetic acid, phosphoric acid and malic acid to give compound (XI). Preferred reaction solvents include benzenee and toluene, and the reaction carried out under in the range from 70° C. up to 110° C.

[Scheme 2]

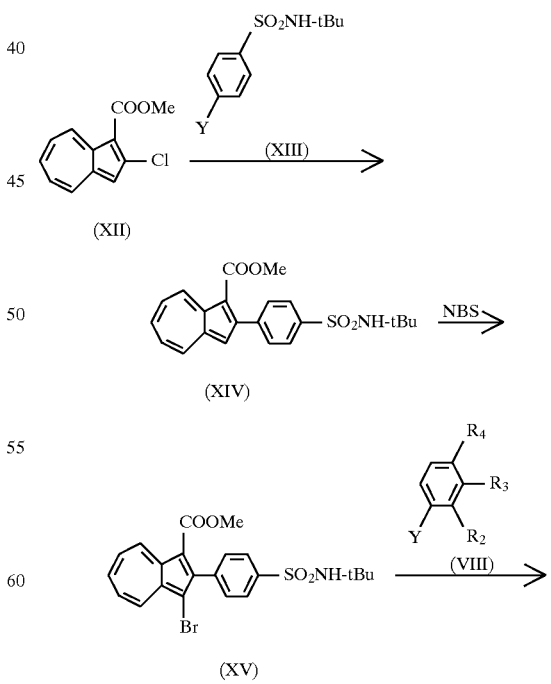

-continued
[Scheme 2]

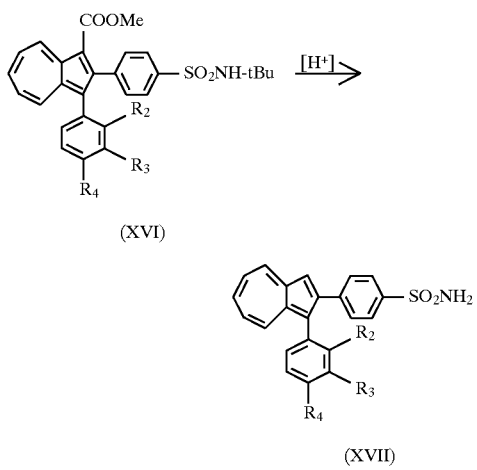

(wherein $R_2$, $R_3$, $R_4$ and Y are the same as mentioned above.)

Scheme 2 shows the preparation of sulfonamide derivatives. Compound (XIII) is synthesized according to the reported methods (Journal of organic chemistry, 40, 1689, 1975). In step 1, compound (XII) is coupled with compound (XIII) to give the compound (XIV). In the case of Y being $B(OH)_2$ in the formula (XIII), the reaction is carried out using palladium catalyst in the presence of base according to reported methods (Synthetic communications, 11, 513, 1981). Tetrakis (triphenylphosphine) palladium (0), bis (triphenylphosphine) palladium chloride (2) and palladium chloride (2) can be used as a catalyst. This reaction carried out in the presence of base such as sodium hydrogencarbonate, sodium carbonate, sodium methoxide, triethylamine and pyridine. Preferred reaction solvents for use in this coupling include benzenee, toluene, dioxane, tetrahydrofuran, chloroform, methanol, N, N-dimethylformamide and water. In general, this reaction carried out under the reflux temperature of the reaction mixture. Alternatively, compound (XIV) can be obtained using the tin reagent instead of boronic acid. In the case of Y being $SnMe_3$ in the formula (XIII), the reaction is carried out using palladium catalyst according to reported methods (Angewante chimie, international edition in English, 25, 508, 1986). Tetrakis (triphenylphpsphine) palladium (0), bis(triphenylphosphine)palladium chloride (2) and palladium chloride (2) can be used as catalysts. Preferred reaction solvents for use in this coupling include benzenee, toluene, dioxane, tetrahydrofuran, chloroform, methanol, N, N-dimethylformamide and water. In general, this reaction carried out under the reflux temperature of the reaction mixture. In step 2, the bromination of compound (XIV) using N-bromsuccinimide or bromine give the compound (XV). This reaction is carried out in the presence of radical initiators such as α,α'-azobis(isobutyronitrile) and benzoylperoxide in carbon tetrachloride as a reaction solvent under the reflux temperature of the reaction mixture. In step 3, compound (XV) is coupled with compound (VII) to give compound (XVI). In the case of Y being $B(OH)_2$ in the formula (VIII), the reaction is carried out using palladium catalyst in the presence of base according to reported methods (Synthetic communications, 11, 513, 1981). Tetrakis (triphenylphosphine) palladium (0), bis (triphenylphosphine) palladium chloride (2) and palladium chloride (2) can be used as catalysts. This reaction carried out in the presence of bases such as sodium hydrogencarbonate, sodium carbonate, sodium methoxide, triethylamine and pyridine. Preferred reaction solvents for use in this coupling include benzenee, toluene, dioxane, tetrahydrofuran, chloroform, methanol, N, N-dimethylformamide and water. In general, this reaction carried out under the reflux temperature of the reaction mixture. Alternatively, compound (XVI) can be obtained using a tin reagent instead of boronic acid. In the case of Y being $SnMe_3$ in the formula (VIII), the reaction is carried out using palladium catalyst according to reported methods (Angewante chimie, international edition in English, 25, 508, 1986). Tetrakis (triphenylphosphine) palladium (0), bis( triphenylphosphine) palladium chloride (2) and palladium chloride (2) can be used as catalysts. Preferred reaction solvents for use in this coupling reaction include benzenee, toluene, dioxane, tetrahydrofuran, chloroform, methanol, N, N-dimethylformamide and water. In general, this reaction carried out under the reflux temperature of the reaction mixture. In step 4, demethoxycarbonylation of compound (XVI) under acidic conditions proceeds and take place simultaneously with deprotection of the t-butyl group to give the compound (XVII). Sulfuric acid, p-toluenesulfonic acid, trifluoroacetic acid and phosphoric acid are suitable for acids and the reaction carried out in reaction solvents as benzenee or toluene under the reflux temperature of the reaction mixture.

[Scheme 3]

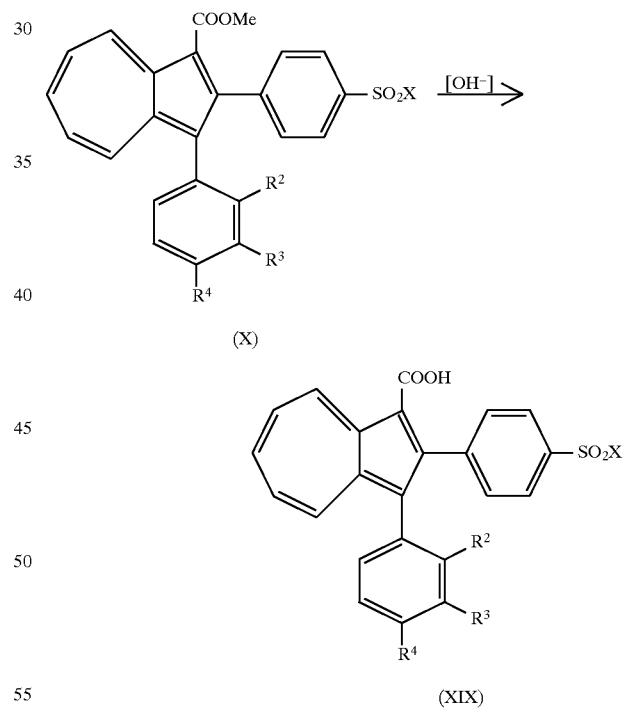

(wherein $R_2$, $R_3$, $R_4$ and X are the same as mentioned above.)

Scheme 3 shows the preparation of carboxylic acid derivatives. Compound (X), which is synthesized in scheme 1, is hydrolyzed under basic conditions to give the compound (XIX). The aqueous solutions of sodium hydroxide, potassium hydroxide or lithium hydroxide can be employed for the hydrolysis and this reaction is carried out in reaction solvents such as methanol, ethanol, tetrahydrofuran or dioxane under the reflux temperature of the reaction mixture.

[Scheme 4]

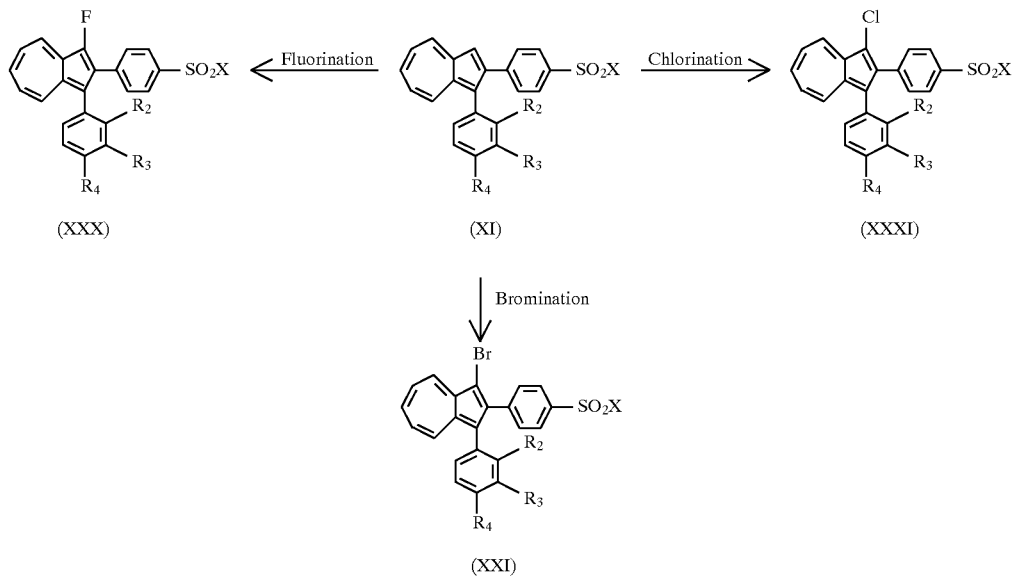

(wherein $R_2$, $R_3$, $R_4$ and X are the same as mentioned above.)

Scheme 4 shows the preparation of 1-halogenated azulene derivatives. Fluorination of compound (XI), which is synthesized in scheme 1, give the compound (XXX). 1-Fluoropyridinium triflate is suitable for a fluorinated agent and this reaction is carried out in 1, 2-dichloroethane as reaction solvents under the reflux temperature of the reaction mixture. Compounds (XXXI) and (XXI) are prepared by halogenation of compound (XI) with N-chlorosuccinimide, N-bromosuccineimide or bromine. This reaction is carried out in the presence of radical initiators such as $\alpha,\alpha'$-azobis (isobutyronitrile) and benzoylperoxide in carbon tetrachloride as a reaction solvent under the reflux temperature of the reaction mixture.

Scheme 5 shows the preparations of 1-alkyl and 1-phenylazulene derivatives. The reaction of compound (XXI) with methylboronic acid or phenylboronic acid give the compounds (XXXII) or (XXXIII). The reaction is carried out using the palladium catalyst in the presence of base according to reported methods (Synthetic communications, 11, 513, 1981). Tetrakis (triphenylphosphine) palladium (0), bis (triphenylphosphine) palladium chloride (2) and palladium chloride (2) can be used as catalysts. This reaction carried out in the presence of bass such as sodium hydrogencarbonate, sodium carbonate, sodium methoxide, triethylamine and pyridine. Preferred reaction solvents for use in this coupling reaction include benzenee, toluene, dioxane, tetrahydrofuran, chloroform, methanol, N, N-dimethylformamide and water. In general, this reaction

[Scheme 5]

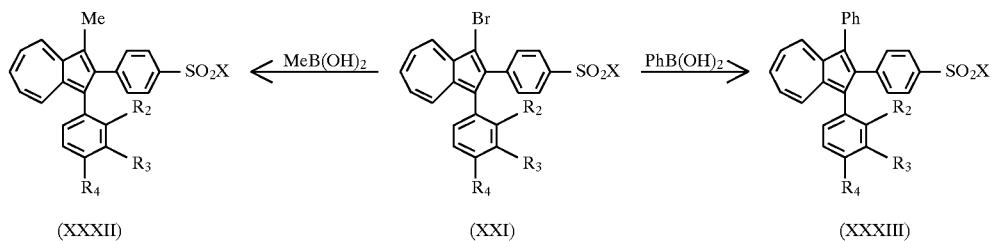

(wherein $R_2$, $R_3$, $R_4$ and X are the same as mentioned above.)

carried out under the reflux temperature of the reaction mixture.

[Scheme 6]

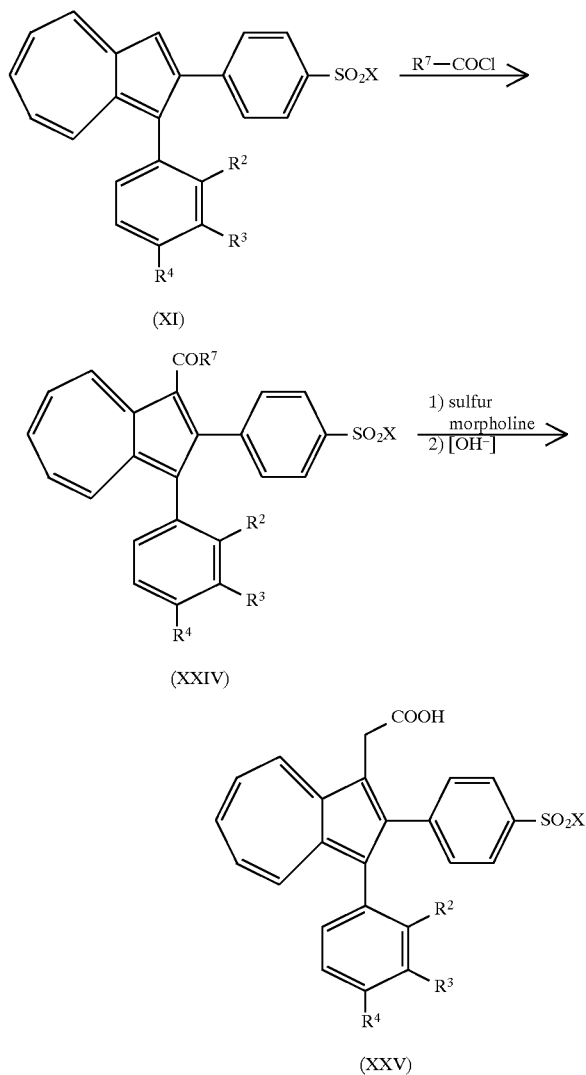

(XI)

(XXIV)

(XXV)

(wherein $R_2$, $R_3$, $R_4$ and X are the same as mentioned above; $R_7$ is methyl group)

Scheme 6 shows the preparations of 1-acylazulene and azulene-1-acetic acid derivatives. In step 1, compound (XI), which is synthesized in scheme 1, is acylated by Friedel-crafts reaction to give the compound (XXIV). The acid chloride can be used as acylated agents and this reaction carried out in the presence of Lewis acids such as aluminium chloride, titanium tetrachloride, tin tetrachloride or boron trifluoride in reaction solvents as dichloromethane, 1, 1, 2, 2-tertachlroethane carbondisulfide and nitrobenzenee under the reflux temperature of the reaction mixture. In step 2, Wiligerodt-kindler reaction of compound (XXIV) give the compound (XXV). Wilgerodt-kindler reaction is carried out using sulfur in the presence of secondary amines such as dimethylamine, morpholine or piperidine. The obtained thioamide derivatives are hydrolyzed under acid or basic conditions to give the compound (XXV). The aqueous solutions of hydrochloride, sulfonic acid, sodium hydroxide, potassium hydroxide and lithium hydroxide are suitable for this hydrolysis and the reaction carried out in reaction solvents as methanol, ethanol, tetrahydrofuran and dioxane under the reflux temperature of the reaction mixture.

The reaction products are purified as free acids or pharmaceutically acceptable alkali-addition salts using extraction, concentration, evaporation, crystallization, filtration, recrystallization, chromatography etc.

The compounds of the present invention may be administered alone or in combination with pharmaceutically acceptable carriers or diluents (diluents: soluble starch, lactose, sucrose, calcium carbonate, calcium phosphate; binders: soluble starch, acacia, carboxymethylcellulose, hydroxymethylcellulose, crystalline cellulose, alginic acid, gelatin, polyvinylpyridone; lubricants: stearic acid, magnesium stearate, calcium stearate, talc; disintegrants: carboxymethylcellulose, talc; pharmaceutical solvents: saline). They may be combined with various pharmaceutically acceptable inert carriers in the form of powders, granule subtilaes, tablets, capsules, external applications and injections.

They can be administered orally. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 50 mg to 5 g. Preferably 100 mg to 500 mg per day given in divided doses 1 to 3 times a day. The example of dosage are 10 mg, 50 mg, 100 mg, 200 mg, 500 mg and 1 g.

PHARMACOLOGICAL EXPERIMENT

Pharmacological experiment are as follows. Inhibitory activity of compounds on COX-1 and COX-2 were assayed according to the method of Needleman (J. Biol. Chem., 254, 9772, 1979). One unit of COX-1 or COX-2 enzyme, suspended with Tris-HCl buffer (pH 8.0, 500 $\mu$l) containing 1 $\mu$M hematin as co-factor, was incubated with compound and 1 mM arachidonic acid at 37° C. for 10 min. The reaction was stopped with 50 mM indomethacin (50 $\mu$l), and amounts of $PGE_2$ in the reaction mixture was assayed using $PGE_2$ ELISA system. $IC_{50}$ (the concentrations which inhibited $PGE_2$ production by 50 %) were calculated and shown in Table 1.

TABLE 1

| Compound | COX-1 $IC_{50}$ ($\mu$M) | COX-2 $IC_{50}$ ($\mu$M) |
| --- | --- | --- |
| 1 | >10 | 0.76 |
| 2 | >10 | 6.9 |
| 3 | >10 | 0.0093 |
| 4 | >10 | 0.030 |
| 5 | >10 | >10 |
| 6 | >10 | 1.2 |
| 7 | >10 | 0.048 |
| 8 | >10 | 7.4 |
| 9 | >10 | 4.8 |
| 10 | >10 | 3.7 |
| 11 | >10 | 0.083 |
| 12 | >10 | 0.0049 |
| 13 | >10 | 0.019 |
| 14 | >10 | 0.0084 |
| 21 | >10 | 7.9 |
| 27 | >10 | 0.0086 |
| 28 | 7.6 | 2.6 |
| 29 | 4.7 | 0.77 |
| 30 | 4.3 | 0.50 |
| 31 | >10 | 2.5 |
| 32 | >10 | 0.012 |
| 33 | 4.1 | 0.0026 |
| 34 | 0.96 | 0.0034 |
| 35 | 6.7 | 0.022 |
| 38 | >10 | 0.064 |
| 39 | >10 | 0.29 |

EFFECTIVENESS OF THE INVENTION

This invention is in the field of antiinflammatory pharmaceutical agents and specifically related to compound of general formula (I), compositions and methods for treating inflammation and inflammation-associated disorders. The compound of general formula (I) is useful for treatment of inflammation without NSAIDs-associated side effects such as gastrointestinal irritation and suppression of renal function.

The enzymatic activity of COX involves bis-oxygenation of arachidonic acid to $PGG_2$, which is further reduced to $PGH_2$ in a peroxidase reaction by the same protein. NSAIDs prevent the production of PGs by inhibiting the enzyme COX. Recently, two distinct forms of COX enzyme were distinguished, a constitutive COX-1 enzyme and an inducible form of the enzyme, now commonly known as COX-2. The COX-1 enzyme is expressed in normal tissues and is physiologically important for gastrointestinal and renal functions, while the previously unidentified COX-2 isoform is found to be located primary in inflamed tissues. It seems reasonable that a selective COX-2 inhibitor could block PG production at the site of inflammation without affecting beneficial PGs in normal tissues such as stomach and renal. On the one hand, compounds in this invention are expected to have a usefulness for cancer therapy. Especially, it is thought that these compounds, as like other inhibitors of PG biosynthesis, inhibits the metastasis of benign or partially transformed colon polyp (Acta histochemica suppementband, 29, 195, 1990). Furthermore, COX-2 inhibitors reduce the risks of colonectal carcinoma, and it is reported that COX-2 is highly expressed in apoptosis. From these findings, it is expected to use of COX-2 inhibitors for cancer and apoptosis therapy (Cell, 83, 345, 1995).

REFERENTIAL EXAMPLE

Example 1

2-(4-Methylsulfonylphenyl)-1-phenylazulene (Compound 1)

Methyl 2-(4-methylsulfonylphenyl)-3-phenylazulene-1-carboxylate(0.13 g) was treated with 100% phosphoric acid (5.0 ml). After stirring for 10 min at 120° C., the reaction mixture was poured into ice-water, followed by extracted with EtOAc. The combined EtOAc extracts were washed with water and brine, dried over $Na_2SO_4$ and concentrated. The crude product was purified by $SiO_2$ column chromatography (benzenee/$Et_2O$, 50: 1) to give the title compound (0.10 g) as violet crystals; mp 139°–140° C.

$^1$H NMR ($CDCl_3$):δ=3.07 (3H, s), 7.15 (1H, t), 7.21 (1H, t), 7.31 (2H, d), 7.38–7.45 (3H, m), 7.57–7.62 (4H, s+m), 7.84 (2H, d), 8.28 (1H, d), 9.39 (1H,d).

Example 2–15

The listed compounds 2–14 and 38 in Table 2 were prepared according to the procedure as example 1.

Example 16

Methyl 2-(4-methylsulfonylphenyl)-3-phenylazulene- 1 -carboxylate (Compound 15)

(a) Methyl 2-(4-methylthiophenyl)azulene-1-carboxylate: 3-Methoxycarbonyl-2H-cyclohepta [b] furan-2-one (2.00 g) and 1-(4-methylthiophenyl)-1-trimethylsilyloxy)ethylene (9.30 g) was stirred at 190° C. for 18 hr. The reaction mixture was poured into 10% aqueous HCl, followed by extracted with EtOAc . The combined EtOAc extracts were washed with water, saturated aqueous $NaHCO_3$ and brine, dried over $Na_2SO_4$ and concentrated. The crude product was purified by $SiO_2$ column chromatography (EtOAc/n-hexane, 1:10) to give the tide compound (2.70 g) as violet crystals; mp 101°–102° C.

$^1$H NMR ($CDCl_3$):δ=2.55 (3H, s), 3.81 (3H, s), 7.31–7.34 (4H, m), 7.42 (1H, t), 7.50–7.55 (2H, m), 7.52 (2H,d), 7.73 (1H, t), 8.38 (1H, d), 9.37 (1H, d).

(b) Methyl $^3$-bromo-2-(4-methylthiophenyl)azulene-1-carboxylate: To a solution of 2-(4-methylsulfonylphenyl)-1-phenylazulene (2.00 g) in $CCl_4$ (20.0 ml) was added N-bromosuccinimide (1.26 g) and α,α'-azobis (isobutyronitrile) (0.01 g), and the reaction mixture was heated under reflux for 1 hr. The mixture was filtered, and concentrated. The crude product was purified by $SiO_2$ column chromatography (benzene/$Et_2O$, 100:1) to give the title compound (2.40 g) as violet crystals; mp 98°–100° C.

$^1$H NMR ($CDCl_3$):δ=2.56 (3H, s), 3.71 (3H, s), 7.33–7.40 (4H, m), 7.57 (1H, t), 7.59 (1H, t), 7.83 (1H, t), 8.60 (1H, d), 9.46 (1H, d).

(c) Methyl 2-(4-methylthiophenyl)-3-phenylazulene-1-carboxylate: To a solution of methyl 3-bromo-2-(4-methylthiophenyl)azulene-1-carboxylate (0.50 g) in toluene (20.0 ml) was added phenylboronic acid (0.38 g), tetrakis (triphenylphosphine)palladium (0) (0.08 g) and 2M aqueous $Na_2CO_3$ (2.6 ml), and the reaction mixture was heated under reflux for 2 hr. The mixture was poured into ice-water, followed by extracted with EtOAc. The combined EtOAc extracts were washed with water and brine, dried over $Na_2SO_4$, and concentrated. The crude product was purified by $SiO_2$ column chromatography (benzenee/EtOAc, 100:1) to give the title compound (0.49 g) as violet crystals; mp 115°–116° C.

$^1$H NMR ($CDCl_3$):δ=2.48 (3H, s), 3.66 (3H, s), 7.10–7.38 (7H, m), 7.39 (2H, d), 7.58 (1H, t), 7.80 (2H, d), 8.36 (1H, d), 9.47 (1H, d).

(d) Methyl 2-(4-methylsulfonylphenyl)-3-phenylazulene-1-carboxlate: To a solution of methyl 2-(4-methylthiophenyl)-3-phenylazulene-1-carboxylate (0.60 g) in MeOH (10.0 ml) was added a solution of oxone (1.90 g) in water (10.0 ml), and the reaction mixture was stirred at room temperature for 16 hr, followed by extracted with EtOAc. The combined EtOAc extracts were washed with brine, dried over $Na_2SO_4$, and concentrated. The crude product was purified by $SiO_2$ column chromatography ($CHCl_3$/acetone, 100:1) to give the title compound (0.54 g) as green crystals; mp 69°–70° C.

$^1$H NMR ($CDCl_3$):δ=3.07 (3H, s), 3.73 (3H, s), 7.11–7.36 (7H, m), 7.41 (2H, d), 7.60 (1H, t), 7.83 (2H, d), 8.41 (1H, d), 9.56 (1H, d).

Example 17

2-(4-Methylsulfonylphenyl)-3-phenylazulene-1-carboxylic acid (Compound 16)

To a solution of methyl $^2$-(4-methylsulfonylphenyl)-3-phenylazulene-1-carboxylate (0.26 g) in MeOH (10.0 ml) was added 10% aqueous NaOH (2.0 ml), and the reaction mixture was heated under reflux for 6 hr. After removal of solvent, the aqueous layer was washed with $Et_2O$. The solution was adjusted to pH 2.0 with 10% aqueous HCl, and extracted with EtOAc. The combined EtOAc extracts were washed with water and brine, dried over $Na_2SO_4$, and concentrated. The crude product was purified by $SiO_2$ column chromatography (EtOAc/MeOH, 30: 1) to give the title compound (0.20 g) as violet crystals; mp 168°–169° C.

$^1$H NMR ($CDCl_3$):δ=3.23 (3H, s), 7.17 (2H, d), 7.30–7.37 (3H, m), 7.45 (2H, d), 7.58 (1H, t), 7.71 (1H, t), 7.80 (2H, d), 7.98 (1H, t), 8.33 (1H, d), 9.55 (1H, d), 12.35 (1H, bs).

Example 18–22

The listed compounds 17–20 and 36 in Table 2 were prepared according to the procedure as example 17.

Example 23

1-Fluoro-2-(4-methylsulfonylphenyl)-3-phenylazulene (Compound 21)

To a solution of 2-(4-methylsulfonylphenyl)-1-phenylazulene (0.20 g) in 1, 2-dichloroethane (20.0 ml) was added 1-fluoropyridinium triflate (0.28 g), and the reaction mixture was heated under reflux for 30 min. The mixture was poured into ice-water, and extracted with $CHCl_3$. The combined $CHCl_3$ extracts were washed with water and brine, dried over $Na_2SO_4$, and concentrated. The crude product was purified by $SiO_2$ column chromatography (benzenee/EtOAc, 20:1) to give the title compound (0.10 g) as green crystals; mp 120°–122° C.

$^1$H NMR (CDCl$_3$):δ=3.08 (3H, s),7.01 (2H, t), 7.06 (1H, t), 7.25–7.28 (2H, m), 7.37–7.43 (2H, m), 7.55 (1H, t), 7.61 (2H, d), 7.87 (2H, d), 8.22 (1H, d,d), 8.35 (1H, d).

Example 24

1-Chloro-2-(4-methylsulfonylphenyl)-3-phenylazulene (Compound 22)

To a solution of 2-(4-methylsulfonylphenyl)-1-phenylazulene (0.20 g) in $CCl_4$ (10.0 ml) was added N-chlorosuccinimide (0.08 g) and α,α'-azobis (isobuthyronitrile) (0.01 g), and the reaction mixture was heated under reflux for 1 hr. The mixture was filtered, and concentrated. The crude product was purified by $SiO_2$ column chromatography (benzene/EtOAc, 20:1) to give the title compound (0.10 g) as green crystals; mp 140°–142° C.

$^1$H NMR (CDCl$_3$):δ=3.09 (3H, s), 7.14–7.38 (7H, m), 7.58 (2H, d), 7.65 (1H, t), 7.89 (2H, d), 8.29 (1H, d), 8.52 (1H, d).

Example 25

1-Bromo-2-(4-methylsulfonylphenyl)-3-phenylazulene (Compound 23)

To a solution of 2-(4-methylsulfonylphenyl)-1-phenylazulene (0.43 g) in $CCl_4$ (20.0 ml) was added N-bromosuccinimide (0.23 g) and α,α'-azobis (isobutyronitrile) (0.01 g), and the reaction mixture was heated under reflux for 1 hr. The mixture was cooled to room temperature and was filtered, and concentrated. The crude product was purified by $SiO_2$ column chromatography (benzene/EtOAc, 20:1) to give the title compound (0.52 g) as green crystals; mp 172°–173° C.

$^1$H NMR (CDCl$_3$):δ=3.10 (3H, s), 7.17–7.37 (7H, m), 7.56 (2H, d), 7.67 (1H, t), 7.89 (2H, d), 8.29 (1H, d), 8.53 (1H, d).

Example 26

1- Methyl-2-(4-methylsulfonylphenyl)-3-phenylazulene (Compound 24)

To a solution of methyl 1-bromo-2-(4-methylsulfonylphenyl)-3-phenylazulene (0.20 g) in toluene (10.0 ml) was added methylboronic acid (0.13 g), tetrakis (triphenylphosphine)palladium (0) (0.05 g) and 2M aqueous $Na_2CO_3$ (0.9 ml), and the reaction mixture was heated under reflux for 2 hr. The reaction mixture was poured into ice-water, followed by extracted with EtOAc. The combined EtOAc extracts were washed with water and brine, dried over $Na_2SO_4$, and concentrated. The crude product was purified by $SiO_2$ column chromatography (benzenee/EtOAc, 20: 1) to give the title compound (0.15 g) as violet crystals; mp 165°–167° C.

$^1$H NMR (CDCl$_3$):δ=3.03 (3H, s), 7.12–7.39 (14H, m), 7.59 (1H, t), 7.66 (2H, d), 8.35 (2H, d).

Example 27

The listed compounds 25 in Table 2 were prepared according to the procedure as example 26.

Example 28

1-Acetyl-2-(4-methylsulfonylmethyl)-3-phenylazulene (Compound 26)

To a solution of 2-(4-methylsulfonylphenyl)-1-phenylazulene (0.13 g) in $CH_2Cl_2$ (10.0 ml) was added anhydrous $AlCl_3$ (0.07 g) at 0° C., and the reaction mixture was stirred for 30 min at same temperature. Then, acetyl chloride (0.04 ml) was added at same temperature, and the reaction mixture was heated under reflux for 8 hr. The mixture was poured into ice-water, and extracted with EtOAc. The combined EtOAc extracts were washed with water, saturated aqueous $NaHCO_3$ and brine, dried over $Na_2SO_4$, and concentrated. The crude product was purified by $SiO_2$ column chromatography (benzenee/EtOAc, 10:1) to give the title compound (0.12 g) as violet crystals; mp 138°–139° C.

$^1$H NMR (CDCl$_3$):δ=2.10 (3H, s), 3.09 (3H, s), 7.14 (2H, dd), 7.13–7.35 (8H, m), 7.42 (1H, t), 7.47 (2H, d), 7.59 (1H, t), 7.82 (1H, t), 7.89 (2H, d), 8.39 (1H, d), 9.42 (1H, d).

Example 29

4-(1 -Phenylazulene-2-yl)phenylsulfonamide (Compound 27)

(a) Methyl 2-(4-t -butylaminosulfonylphenyl) azulene-1-carboxylate: To a solution of methyl 2-chloroazulene-1-carboxylate (0.50 g) in toluene (20.0 ml) was added 4-t-butylaminosulfonyl-phenylboronic acid (0.87 g), tetrakis (triphenylphosphine)palladium (0) (0.12 g), and 2M aqueous $Na_2CO_3$ (4.5 ml), and the reaction mixture was heated under reflux for 16 hr. The mixture was poured into ice-water, followed by extracted with EtOAc. The combined EtOAc extracts were washed with water and brine, dried over $Na_2SO_4$, and concentrated. The crude product was purified by $SiO_2$ column chromatography (CHCl$_3$/EtOAc, 100:1) to give the title compound (1.13 g) as violet crystals; mp 169°–170° C.

$^1$H NMR (CDCl$_3$):δ=1.29 (9H, s), 3.74 (3H, s), 4.57 (1H, bs), 7.34 (1H, s), 7.49 (1H, t), 7.60 (1H, t), 7.65 (2H, d), 7.82 (1H, t), 7.95 (2H, d), 7.45 (1H, d), 9.52 (1H, d).

(b) Methyl 3-bromo-2-(4-t-butylaminosulfonylphenyl) azulene-1-carboxylate: To a solution of 2-(4-t -butylaminosulfonylphenyl) -1-phenylazulene (0.50 g) in $CCl_4$ (20.0 ml) was added N-bromosuccinimide (0.25 g) and α,α'-azobis (isobutyronitrile) (0.01 g), and the reaction mixture was heated under reflux for 1 hr. The reaction mixture was filtered, and concentrated. The crude product was purified by $SiO_2$ column chromatography (benzene/ EtOAc, 20:1) to give the title compound (0.56 g) as violet crystals; mp 171°–172° C.

$^1$H NMR (CDCl$_3$):δ=1.30 (9H, s), 3.62 (3H, s), 4.59 (1H, bs), 7.53 (2H, d), 7.63 (1H, t), 7.66 (1H, t), 7.91 (1H, t), 7.99 (2H, d), 8.64 (1H, d), 9.52 (1H, d).

(c) Methyl 2-(4-t-butylaminosulfonylphenyl)-3-phenylazulene-1-carboxylate: To a solution of methyl 3-bromo-2-(4-t-butylaminosulfonylphenyl) azulene-1-carboxlate (0.56 g) in toluene (10.0 ml) was added phenylboronic acid (0.34 g), tetrakis(triphenylphosphine) palladium (0) (0.07 g) and 2M aqueous $Na_2CO_3$ (2.3 ml), and the reaction mixture was heated under reflux for 2 hr. The reaction mixture was poured into ice-water, followed by extracted with EtOAc. The combined EtOAc extracts were washed with water and brine, dried over $Na_2SO_4$, and concentrated. The crude product was purified by $SiO_2$ column chromatography (benzenee/EtOAc, 20:1) to give the title compound (0.47 g) as violet crystals; mp 76°–77° C.

$^1$H NMR ($CDCl_3$):δ=1.21 (9H, s), 3.66 (3H, s ), 4.44 (1H, bs),7.11–7.28 (5H, m), 7.31 (2H, d), 7.42 (1H, t), 7.56 (1H, t), 7.78 (2H, d), 7.82 (1H, t), 8.42 (1H, d), 9.62 (1H,d).

(d) 4-(1-Phenylazulene-2-yl)phenylsulfonamide (Compound 27): A mixture of methyl 2-(4-t-butylaminosulfonylphenyl)-3-phenylazulene-1-carboxlate (0.46 g) and 100% phosphoric acid (12.0 ml) was heated and stirred at 110° C. for 10 min. The reaction mixture was poured into ice-water, and extracted with EtOAc. The combined EtOAc extracts were washed with water and brine, dried over $Na_2SO_4$, and concentrated. The crude product was purified by $SiO_2$ column chromatography ($CHCl_3$/acetone, 20:1) to give the title compound (0.25 g) as green crystals; mp 188°–189° C.

$^1$H NMR ($CDCl_3$):δ=4.80 (2H, bs), 7.15 (1H, t), 7.20 (1H, t), 7.30–7.44 (5H, m), 7.54–7.62 (2H, s+t), 7.56 (2H, d), 7.82 (2H, d), 8.27 (1H, d), 8.38 (1H, d Example 30–38: The listed compounds 28–35 and 39 in Table 2 were prepared according to the procedure as example 29.

TABLE 2

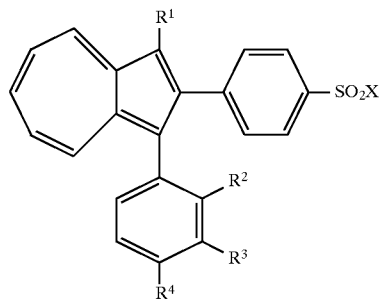

| Compounds | $R^1$ | $R^2$ | $R^3$ | $R^4$ | X | Melting point (°C.) |
|---|---|---|---|---|---|---|
| 1 | H | H | H | H | Me | 164–165 |
| 2 | H | Cl | H | H | Me | 175–176 |
| 3 | H | H | Cl | H | Me | 155–156 |
| 4 | H | H | H | Cl | Me | 187–188 |
| 5 | H | H | F | H | Me | 140–141 |
| 6 | H | H | H | F | Me | 151–152 |
| 7 | H | H | Me | H | Me | 146–147 |
| 8 | H | H | H | Me | Me | 178–179 |
| 9 | H | H | OMe | H | Me | 188–189 |
| 10 | H | H | H | OMe | Me | 180–181 |
| 11 | H | H | Cl | F | Me | 188–189 |
| 12 | H | H | Cl | Me | Me | 197–199 |
| 13 | H | H | Cl | OMe | Me | 204–205 |
| 14 | H | H | F | OMe | Me | 191–192 |
| 15 | COOMe | H | H | H | Me | 112–113 |
| 16 | COOH | H | H | H | Me | 168–169 |
| 17 | COOH | H | Cl | H | Me | 190–192 |
| 18 | COOH | H | Cl | Me | Me | 203–205 |
| 19 | COOH | H | Cl | OMe | Me | 231–232 |
| 20 | COOH | H | F | OMe | Me | 215–216 |

TABLE 2-continued

| Compounds | $R^1$ | $R^2$ | $R^3$ | $R^4$ | X | Melting point (°C.) |
|---|---|---|---|---|---|---|
| 21 | F | H | H | H | Me | 120–122 |
| 22 | Cl | H | H | H | Me | 140–142 |
| 23 | Br | H | H | H | Me | 172–173 |
| 24 | Me | H | H | H | Me | 122–123 |
| 25 | Ph | H | H | H | Me | 165–167 |
| 26 | COMe | H | H | H | Me | 138–139 |
| 27 | H | H | H | H | $NH_2$ | 188–189 |
| 28 | H | H | F | H | $NH_2$ | 166–167 |
| 29 | H | H | Cl | H | $NH_2$ | 168–169 |
| 30 | H | H | Me | H | $NH_2$ | 181–182 |
| 31 | H | H | MeO | H | $NH_2$ | 172–173 |
| 32 | H | H | Cl | F | $NH_2$ | 118–119 |
| 33 | H | H | Cl | Me | $NH_2$ | 117–119 |
| 34 | H | H | Cl | OMe | $NH_2$ | 222–223 |
| 35 | H | H | F | OMe | $NH_2$ | 102–103 |
| 36 | COOH | H | Cl | OMe | $NH_2$ | 231–232 |
| 37 | $CH_2COOH$ | H | H | H | Me | 130–132 |
| 38 | H | H | OMe | OMe | Me | 183–184 |
| 39 | H | H | OMe | OMe | $NH_2$ | 222–223 |

What is claimed is:

1. A compound of the general formula (I):

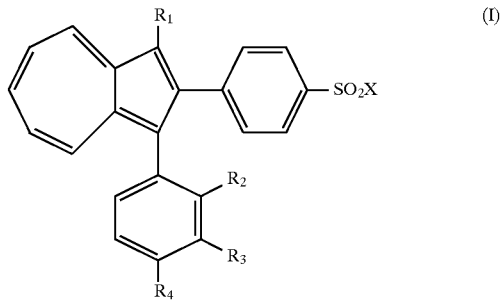

wherein: $R_1$ is hydrogen atom, lower alkoxycarbonyl group, carboxy group, halogen atom, lower alkyl group, phenyl group or lower alkanoyl group; $R_2$, $R_3$ and $R_4$ are hydrogen atom, lower alkyl group, lower alkoxy group or halogen atom; X is lower alkyl group or amino group.

2. A compound of the general formula (II):

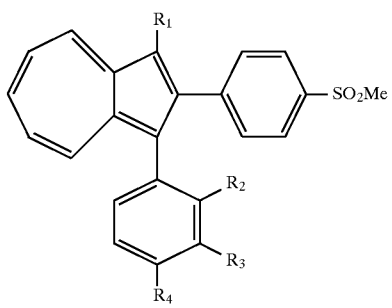

wherein: $R_1$ is hydrogen atom, methoxycarbonyl group, carboxy group, fluorine atom, chlorine atom, bromine atom, methyl group, phenyl group or acetyl group ; $R_2$, $R_3$ and $R_4$ are hydrogen atom, methyl group, methoxy group, fluorine atom or chlorine atom.

3. A compound of the general formula (III):

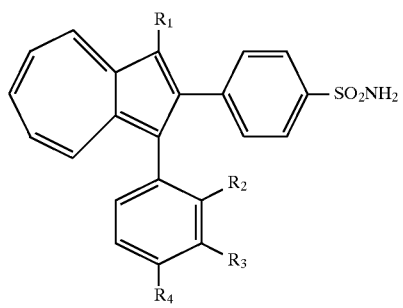

wherein: $R_1$ is hydrogen atom, methoxycarbonyl group, carboxy group, fluorine atom, chlorine atom, bromine atom, methyl group, phenyl group or acetyl group; $R_2$, $R_3$ and $R_4$ are hydrogen atom, methyl group, methoxy group, fluorine atom or chlorine atom.

4. A pharmaceutical composition that is used for the treatment of inflammation, pain and fever, wherein an active ingredient is a compound mentioned in claim 1 to 3.

5. A method of preparing a compound of general formula (XI):

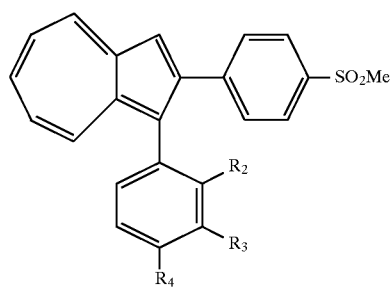

wherein: $R_2$, $R_3$ and $R_4$ are hydrogen atom, methyl group, methoxy group, fluorine atom or chlorine atom;

comprising reacting a compound of general formula (IV):

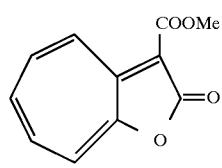

with a compound of general formula (V):

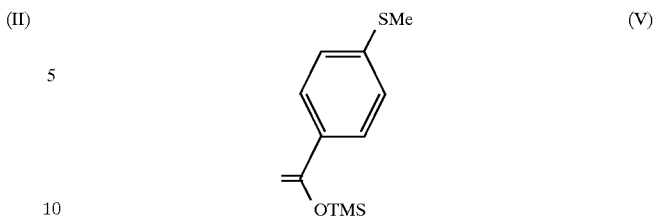

wherein: OTMS represents trimethylsilyloxy group;

to produce a compound of general formula (VI):

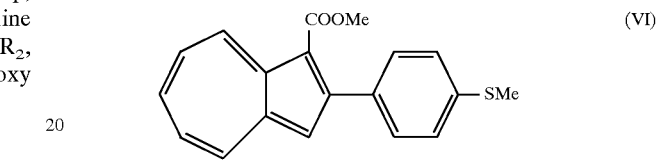

and then a compound of formula (VI) is brominated to produce a compound of formula (VII):

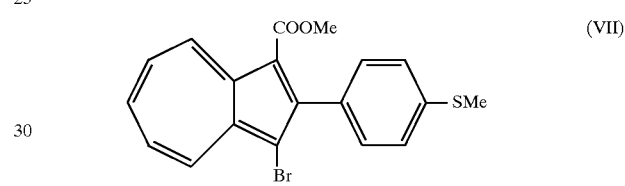

and then a compound of formula (VII) is reacted with a compound of formula (VIII):

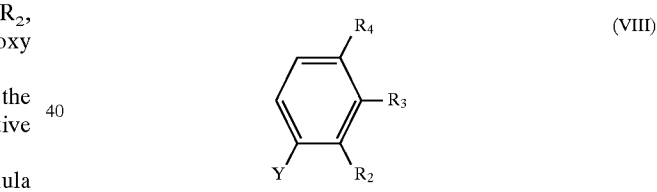

wherein: $R_2$, $R_3$ and $R_4$ are hydrogen atom, methyl group, methoxy group, fluorine atom or chlorine atom; Y is $B(OH)_2$ or $SnMe_3$;

to produce the general formula (IX):

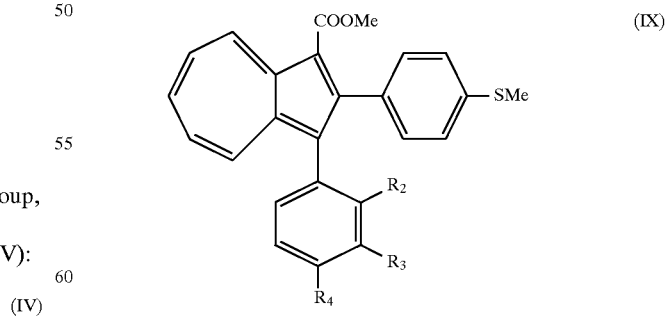

wherein: $R_2$, $R_3$ and $R_4$ are hydrogen atom, methyl group, methoxy group, fluorine atom or chlorine atom;

and then a compound of formula (IX) is oxidized to produce a compound of formula (X):

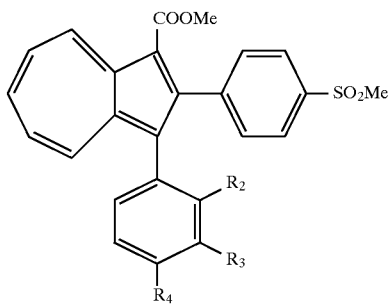

wherein: $R_2$, $R_3$ and $R_4$ are hydrogen atom, methyl group, methoxy group, fluorine atom or chlorine atom;

further the compound (X) is demethoxycarbonylated to produce a compound of formula (XI):

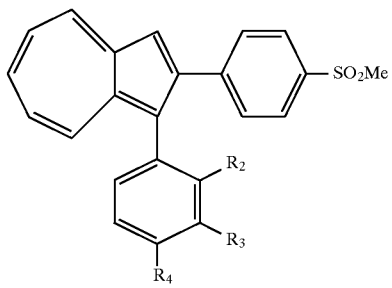

wherein: $R_2$, $R_3$ and $R_4$ are hydrogen atom, methyl group, methoxy group, fluorine atom or chlorine atom.

6. A method of preparing a compound of general formula (XVII):

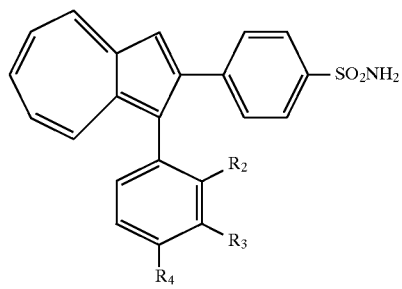

wherein: $R_2$, $R_3$ and $R_4$ are hydrogen atom, methyl group, methoxy group, fluorine atom or chlorine atom;

comprising reacting a compound of general formula (XII):

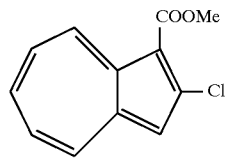

with a compound of the general formula (XIII):

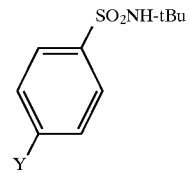

wherein: Y is $B(OH)_2$ or $SnMe_3$;

to produce a compound of general formula (XIV):

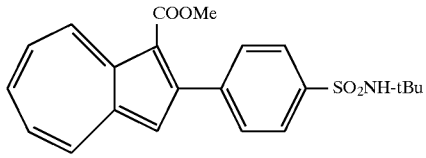

and then a compound of formula (XIV) is brominated to produce a compound of formula (XV):

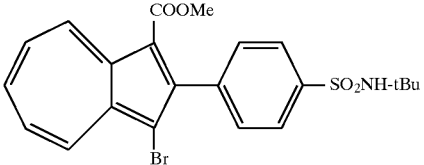

and then a compound of formula (XV) is reacted with a compound of formula (VIII):

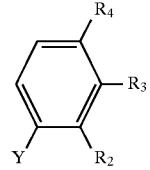

wherein: $R_2$, $R_3$ and $R_4$ are hydrogen atom, methyl group, methoxy group, fluorine atom or chlorine atom; Y is $B(OH)_2$ or $SnMe_3$;

to produce a compound of general formula (XVI):

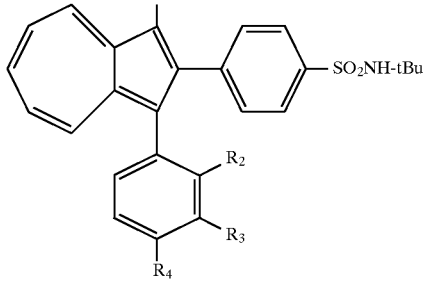

wherein: $R_2$, $R_3$ and $R_4$ are hydrogen atom, methyl group, methoxy group, fluorine atom or chlorine atom;

then the compound (XVI) is demethoxycarbonylated and de-t-butylated to produce the compound of formula (XVII):

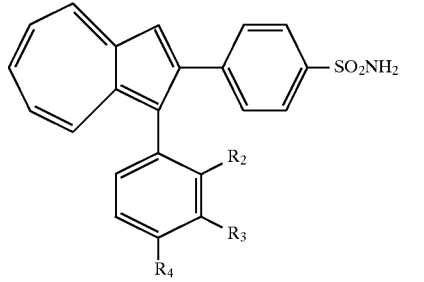

wherein: $R_2$, $R_3$ and $R_4$ are hydrogen atom, methyl group, methoxy group, fluorine atom or chlorine atom.

7. A method of preparing a compound of general formula (XIX):

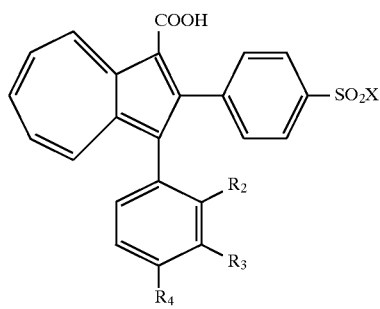

wherein: $R_2$, $R_3$ and $R_4$ are hydrogen atom, methyl group, methoxy group, fluorine atom or chlorine atom; X is lower alkyl group or amino group;

comprising hydrolyzing a compound of general formula (XVIII):

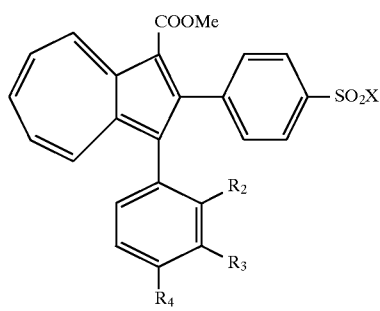

wherein: $R_2$, $R_3$ and $R_4$ are hydrogen atom, methyl group, methoxy group, fluorine atom or chlorine atom; X is lower alkyl group or amino group.

8. A method of preparing a compound of general formula (XX):

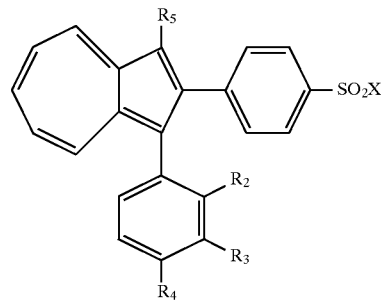

wherein: $R_2$, $R_3$ and $R_4$ are hydrogen atom, methyl group, methoxy group, fluorine atom or chlorine atom; $R_5$ is fluorine atom, chlorine atom or bromine atom; X is lower alkyl group or amino group;

comprising halogenating a compound of general formula (I):

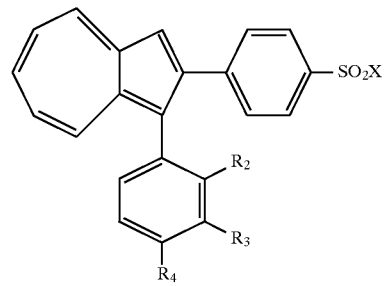

wherein: $R_2$, $R_3$ and $R_4$ are hydrogen atom, methyl group, methoxy group, fluorine atom or chlorine atom; X is lower alkyl or amino group.

9. A method of preparing a compound of general formula (XXIII):

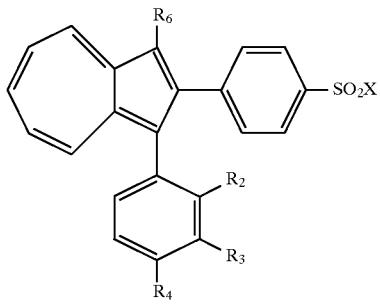

wherein: $R_2$, $R_3$ and $R_4$ are hydrogen atom, methyl group, methoxy group, fluorine atom or chlorine atom ; $R_6$ is methyl group or phenyl group; X is lower alkyl group or amino group;

comprising reacting a compound of general formula (XXI):

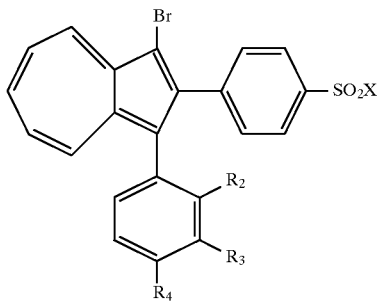

wherein: $R_2$, $R_3$ and $R_4$ are hydrogen atom, methyl group, methoxy group, fluorine atom or chlorine atom; X is lower alkyl group or amino group;

with a compound of general formula (XXII):

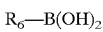

$$R_6\text{—B(OH)}_2 \quad \text{(XXII)}$$

wherein: $R_6$ is methyl group or phenyl group;

to produce a compound of general formula (XXIII):

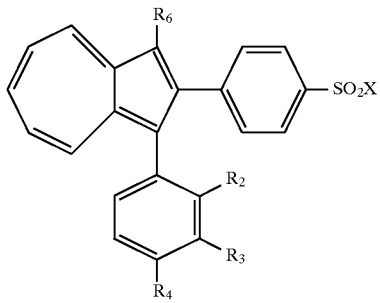

wherein: $R_2$, $R_3$ and $R_4$ are hydrogen atom, methyl group, methoxy group, fluorine atom or chlorine atom ; $R_6$ is methyl group or phenyl group; X is lower alkyl group or amino group.

10. A method of preparing a compound of general formula (XXIV):

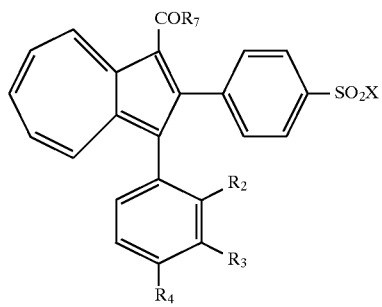

(XXIV)

wherein: $R_2$, $R_3$ and $R_4$ are hydrogen atom, methyl group, methoxy group, fluorine atom or chlorine atom, $R_7$ is methyl group ; X is lower alkyl group or amino group;

comprising reacting a compound of general formula (I) by Friedel-Crafts reaction:

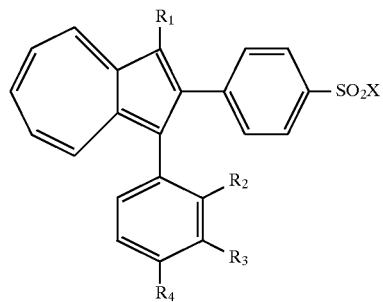

(I)

wherein: $R_1$ is hydrogen atom; $R_2$, $R_3$ and $R_4$ are hydrogen atom, methyl group, methoxy group, fluorine atom or chlorine atom; X is lower alkyl group or amino group.

11. A method of preparing a compound of general formula (XXV):

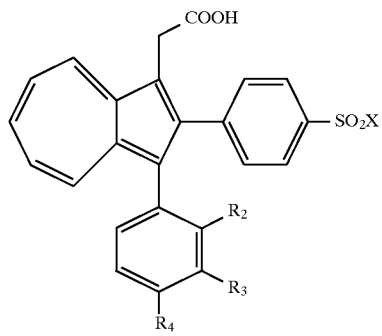

(XXV)

wherein: $R_2$, $R_3$ and $R_4$ are hydrogen atom, methyl group, methoxy group, fluorine atom or chlorine atom; X is lower alkyl group or amino group;

comprising transforming a compound of general formula (XXIV) to thiomorpholide by Willgerodt-Kindler reaction, then hydrolyzing said thiomorpholide:

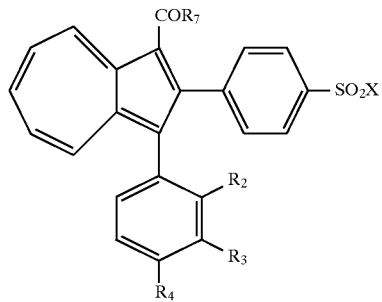

(XXIV)

wherein: $R_2$, $R_3$ and $R_4$ are hydrogen atom, methyl group, methoxy group, fluorine atom or chlorine atom; $R_7$ is methyl group; X is lower alkyl group or amino group.

* * * * *